United States Patent [19]
Brackmann et al.

[11] Patent Number: 5,172,581
[45] Date of Patent: Dec. 22, 1992

[54] METHOD AND APPARATUS FOR ANALYZING ENCAPSULATED VAPORS

[75] Inventors: Richard T. Brackmann; Richard L. Myers, both of Pittsburgh, Pa.; Sanjai K. Bijawat, Boston, Mass.

[73] Assignee: Extrel Corporation, Pittsburgh, Pa.

[21] Appl. No.: 410,506

[22] Filed: Sep. 21, 1989

[51] Int. Cl.⁵ .............................................. G01N 33/00
[52] U.S. Cl. .................................... 73/29.01; 73/19.01
[58] Field of Search ...................... 73/61 R, 52, 29.01, 73/29.05, 19.01

[56] References Cited

U.S. PATENT DOCUMENTS 4,711,118 12/1987 Bossard et al. ..................... 73/52 X

*Primary Examiner*—Hezron E. Williams
*Assistant Examiner*—Joseph W. Roskos
*Attorney, Agent, or Firm*—Penrose Lucas Albright

[57] ABSTRACT

Fluids entrapped in small confined within spaces of an object are analyzed by securing the object containing the confined space by epoxy to a small fitting over a notch applied on the object's surface adjacent to the confined space, the fitting being a slidable seal attached to a small tube which has a piercing device adapted to move with the small tube relative to the fitting and the object containing the confined space to puncture same through the notch, whereby the entrapped gaseous fluid in the confined space emerges into the fitting and small tube, the entire system being a sealed enclosure. Attached to the small tube is a capillary which leads to an analyzing device, such as a mass spectrometer. The small tube fitting and capillary are sufficiently small in volume and configured so that gaseous fluid from the now ruptured confined space flows in a viscous condition from the object to the analyzing device and is in contact with minimal surface area to minimize any adsorption effects which would change the contents of the fluid sample. No elastomer O-rings or other materials known for their adsorption affinities insofar as substances of interest in the contents of the fluid emerging from the confined space are used. A heated chamber may receive the object having the confined space, the small tube including the penetrating device attached thereto and the capillary tube. One valve connected to the tube is provided for purging the system and for admitting calibration gases from an appropriate gas handling system. Confined spaces of interest may be in electronic devices, glasses as well as other solids which entrap fluids that it is desired to analyze.

41 Claims, 5 Drawing Sheets

METHOD AND APPARATUS FOR ANALYZING ENCAPSULATED VAPORS

FIELD OF THE INVENTION

This invention relates to a method and apparatus for breaking a small encapsulated (hermetically confined) volume and introducing the vapor contents, with minimized differential losses due to sorption or chemical reaction, into an analyzer.

OVERVIEW

For a variety of purposes, it is desirable to analyze gaseous constituents of small sealed spaces. For example, in the semiconductor industry, temperature specifications and failure rates of integrated circuit chips correlate with the moisture content of the encapsulated gas. In the glass-making industry, process problems may be diagnosed by analyzing the contents of small bubbles trapped within the product. There is also considerable recent interest in analyzing the content of fossilized amber bubbles to determine the composition of the Earth's early atmosphere.

With the advent of increasingly versatile, sensitive analyzers such as mass spectrometers to analyze confined fluids, an object of interest is hermetically sealed onto an inlet of a pre-evacuated chamber and, without violating the seal, the object is pierced to release the confined fluid into the evacuated chamber, the gaseous contents of which are then drawn into an analyzer. This prior art, pre-evacuated chamber is characteristically large compared to the fluid's confinement volume. Unfortunately, the relatively extensive interior surface area of the pre-evacuated chamber significantly alters comparative abundances of the fluid's various molecular species, prior to analysis, via adsorption, absorption, chemisorption, deabsorption, deadsorption, dechemisorption or chemical reaction with the surfaces. For brevity, "adsorption" is broadly used herein for a process whereby molecules are transformed from an existing vapor phase into a liquid or solid phase, and "desorption" is any process which liberates molecules from a liquid or solid phase transforming them into their vapor phase. Other forms of those terms such as "adsorbed" and "desorbed" are used similarly. "Sorption" and "sorbed" are used generically for both terms in the same broad senses.

The relatively large surface area in the pre-evacuated chamber has particular consequence for species such as water which are also troublesome backgrounds for any analyzer and inlet system. Existing devices for analyzing encapsulated gases require data systems capable of applying extrapolation or integration techniques to compensate for these sorption effects for such "sticky" species as water, such techniques being time-consuming and providing unreliable results. Interface hardware for the existing analysis technology relies on multiple ports and valves for calibrating and evacuating the piercing chamber and uses elastomer O-rings that present strongly sorption-capable surfaces to the fluid and which may provide dead-spaces to the fluid's flow. In addition, any surfaces which can sorb molecules out of the fluid sample can also desorb molecules which have been previously sorbed from the air or from earlier samples. Procedures to minimize the latter of these effects are usually to bake-out the object and chamber in an effort to desorb any previously sorbed molecules. This can unfortunately make the surfaces even more sorbing to molecules from the fluid sample and thus increase the former. An excessive need for carefully controlled baking can also make the overall measurement more cumbersome and time-consuming.

The instant invention embraces a small-volume piercing chamber, with disposable header, that is coupled via a capillary inlet into a mass spectrometer's ionizer. The improvement minimizes the sorption factors by keeping the system sufficiently small that sorption is minimized. In addition, operation at the higher pressure that results from the restraint of the emerging gas to be largely governed by principles applicable to viscous flow regimes, in contrast to regimes characterized by free molecular flow. As a result, at the exit of the piercing chamber of the instant invention, the various molecular and/or atomic species of the fluid flow together at the same velocity and therefore do not separate out in the system, as they would under molecular or transition flow conditions. It is thus possible to calculate the concentrations of selected gaseous species in real-time ratios against one or more further selected constituents (e.g., water against nitrogen in semiconductors), and as much information can be obtained from a single measurement point as would otherwise require an integrated sample in systems where species become spatially separated. Even in the event that in the flow becomes transition or free molecular in subsequent parts of the sampling system, the correct relative concentrations will be maintained if viscous flow predominates at the exit of the piercing chamber. This condition of viscous flow out of the piercing chamber, coupled with the reduced sorption losses, significantly reduce errors in the measured mole-% ratios of relative constituent concentrations, which have been a serious problem in the prior art.

The invention also employs epoxy cements, which sorb very little water and other gases, to be employed where elastomer O-rings (which sorb a great deal of water and other organic molecules) are now used. The invention also permits the piercing volume to be filled with calibration gas, the system calibrated, a device pierced and its contents sampled in minutes. Finally, a disposable piercing header chamber may be pre-baked prior to use on the analyzing system, thereby substantially reducing throughput sample durations by avoiding in-situ bake-out procedures. The result is a simpler, smaller, easier to use interface which eliminates problems with sorption losses and changing flow regimes that are characteristic of earlier systems, and which further significantly reduces time require for individual throughputs and improved productivity.

BACKGROUND OF THE INVENTION

Quantitatively and qualitatively the prior state-of-the-art is illustrated in FIG. 1, where the volume of the piercing chamber is typically of the order of 15 cc and the encapsulated volume typically varies from 0.01 cc to 0.8 cc. The situation is exemplified by the requirements of Method 1018.2 (Internal Water-Vapor Content) of MIL-STD-883B, which calls for measuring water vapor concentrations of 0.5% with an accuracy of ±20% inside ceramic and metal microelectronic packages over the aforementioned volume ranges of 0.01–0.8 cc at an encapsulation pressure of about one atmosphere.

The subsequent discussion will illustrate the difficulties associated with the prior art. Consider a microelectronic device containing an encapsulated, atmospheric-pressure volume of 0.01 cc, containing 0.5% (or 5000 ppm) of water by mole-ratio. This corresponds to about $1.3 \times 10^{15}$ water molecules. When the device is, pierced and its contents emerge into a pre-evacuated 15 cc piercing chamber, the new gas pressure, determined by the ideal gas law, is on the order of $(0.01/15) \times 760$ torr, or about 0.5 torr. This configuration presents a number of difficulties:

(1) A reasonably compact volume of 15 cc has a typical dimension, "d", so that $d=(15)^{.166}=2.5$ cm and a typical internal surface area of the order of $6 \times (2.5)^2 = 38$ cm$^2$. Water molecules are notorious for their propensity to adsorb into almost any surface, and a single monolayer of sorbed water molecules on a perfectly flat surface contains about $5 \times 10^{14}$ molecules/cm$^2$, or $1.8 \times 10^{16}$ molecules in the present illustration. Actual situations are worse; due to microscopic irregularities and pores, the effective surface area may be orders of magnitude larger. It is thus apparent that the internal surface of a typical piercing chamber is capable of sorbing all of the water molecules from the smaller encapsulated chamber wherein the gaseous condition is being analyzed. Conversely, through prior exposure to the atmosphere, the system could easily already be contaminated with as many water molecules as the sample might contain. This represents a source of water molecules that may desorb during analysis to provide an increase of the measured moisture content.

Such problems are very common in analytical chemistry, and particularly in mass spectrometry. Traditional solutions involve the use of glass and/or electropolished metal surfaces to reduce the adverse sorption to monolayer amounts. But, as we have seen, even a monolayer of sorbed molecules may be too much when measuring a minor species of the contents of a very small encapsulation.

In the prior art, these effects can be supposedly minimized by heating the chamber and inlet system. Unfortunately, these efforts are often frustrated because the pre-evacuated heated walls of the chamber/inlet system then exhibit unpredictable sorption activities often with complex hysteresis effects due to the past history of the surfaces One solution is to bake out surfaces in a very reproducible way and to integrate the data over the time required for evacuation of the piercing chamber. Another so-called "dynamic" method is to measure the peak readings of all species just after piercing and attempt to adjust for the fact that sticky molecules such as water are measured at only a small fraction of their true ratio in the original encapsulated sample.

(2) This problem is further greatly compounded by tubing or piping now used to carry the low pressure gas to an analyzer. Because the pressure is low, the tubing must be large in order to provide rapid transport to the analyzer, and this adds still more surface area to the system.

(3) The mean free path for gas molecules at 0.5 torr of pressure is of the order of 0.1 mm, which is a characteristic size of the apertures in valves used to restrict flow into the analyzer to levels compatible with the capacities of their usual vacuum systems. When the mean free path and the aperture sizes are comparable, the flow will be in the transition regime between viscous and free molecular. In free molecular flow, the pumping speed for a gas species is dependent on the molecular velocity, which goes as the inverse square root of the molecular weight. Thus, water is transported more rapidly than, say, oxygen, by the ratio of $(32/18)^{\frac{1}{2}}=1.33$. When the flow is in the transition regime, the separation is less severe but is still observed. This means that, even if sorption/desorption were not a problem, the initial measurement made by the analyzer is erroneous and it is necessary substantially to evacuate almost the entire piercing chamber, measuring and integrating all the while, to obtain a meaningful measurement of the relative abundances of species in the original encapsulated sample.

(4) A typical semiconductor may contain about $10^{-1}$ atmospheric-cc of gas, whereas, for the case of a mass spectrometer, typical vacuum systems handle only about $10^{-4}$ atmospheric-cc/sec of inlet gas load. When different gaseous species get separated via sorption and differing pumping speeds that correspond to transition and molecular-flow regimes, it is necessary to analyze all of the gas from the original device, and this can require most of an hour. Productivity and throughput considerations do not normally permit this.

(5) To seal devices of varying shapes onto the outside of the piercing chamber, characteristically elastomer O-rings or gaskets are used, which sorb substantial amounts of water and certain other gases. Similarly, sealing of the piercing shaft is normally accomplished by using elastomer O-rings. Teflon, which has poor elastic properties, may be used with some risk of leakage, but even Teflon sorbs moisture in the small quantities representative of micro-encapsulation measurements.

To compensate for all of these effects, extrapolation techniques are commonly used. These usually assume that adsorption predominates at the time of piercing, and that thereafter the rate of desorption follows a pattern such that if the water signal is tracked for the first few minutes, the amount of water to desorb over the next few hours can be estimated. But this assumption leads to significant inaccuracies because the sorption properties of a surface are complicated functions of the history of that surface, in terms of its state of porosity, oxidation, temperature, exposure to atmosphere, other absorbed or adsorbed species, etc. In actual practice, the system is calibrated empirically against encapsulated calibration standards that are themselves suspect.

The alternative to encapsulated calibration standards is a dynamic calibration using bottled gases (sometimes humidified with trace amounts of water). The technique used in the prior art usually involves evacuating the piercing chamber via a valved port, flooding it with calibration gas through another port, and then sampling the system through a third valve. The presence of all these valves and ports provides additional surface area and introduces O-rings that will probably sorb water and other sticky molecules and further complicate the analysis even when glass and/or electropolished stainless steel are being used to reduce sorption in the main piercing chamber.

It is thus seen that the prior art, by using a large-volume piercing chamber, creates two problems: (1) the unpredictability of sorption dynamics of the chambers' large internal surfaces, and (2) situations wherein flow regimes in the chambers and their inlets are ambiguous mixes of viscous, transition, and molecular flow.

It is thus apparent that there exists a need for a system that can pierce an encapsulated device and transport its contents to an analyzer without the flow-dependent, species-dependent and concentration-dependent effects recited above and the attendant heroic data acquisition analyses required in attempting to compensate for all these complications. Specifically, it would be highly desirable to eliminate all elastomer O-rings, as much Teflon as possible, as many valves and ports as possible, and to reduce, by at least an order of magnitude, the volume of the piercing chamber.

SUMMARY OF THE INVENTION

The invention described herein provides solutions to all of the problems discussed above by reducing the volume and surface area while raising the pressure in the piercing chamber and subsequent plumbing. In the invention, the volume of the piercing chamber is reduced to about 0.04 cc, or by a factor of 350 less than generally employed in the prior art for the same purpose. The surface area that can contribute to adsorption is consequently reduced to amounts that can be dealt with by judicious choices of materials. Threaded shafts, characteristic of existing piercing pins are replaced by sliding shafts that have very little contact with the gas sample. A single metal-to-metal seating valve is employed to isolate the piercing chamber from all other valves, calibration gas sources and analyzers that could contribute to sorption. Finally, uncertainties about the prior histories of the piercing chambers are further mitigated by providing that the portion of the piercing chamber that seals it to the encapsulation be a small, standard, disposable unit that uses epoxy in place of elastomers.

The present invention also offers the advantage that because pressures in the piercing chamber are relatively high — one hundred, ninety torr in the present example — flow through the tubing that leads to the analyzer is retained in the viscous regime.

Because in viscous flow all molecular species flow together in concert, this comparatively high-pressure transport completely eliminates the potential problem of species separation which happens in prior are transport systems wherein most of the transport tubing is subject to pressures in the transition or molecular flow regimes.

All of these features of the invention, taken together, enable the user to employ a data system that simply takes the real-time ratio of a trace impurity to any second constituent (such as a water-to-nitrogen ratio in the case of semiconductors) for the purpose of calculating relative concentration. The ability to do this in real time minimizes the need to do time-consuming and inaccurate integration and interpolation of the data, thus enhancing accuracy and productivity while reducing cost. It may, of course, still be necessary to perform some extrapolation due to the time required to desorb species that may be sorbed onto the interior surfaces of the encapsulation, but at least the situation is not compounded by sorption dynamics that occur in the piercing chamber/sampling system.

Other objects, adaptabilities and capabilities of the invention will be understood by those skilled in the art from the disclosure of the invention set forth herein and from experience gained from the use of that invention, of reference being had to the accompanying drawings, in which:

DESCRIPTION OF THE PREFERRED EMBODIMENTS

Figure 1:
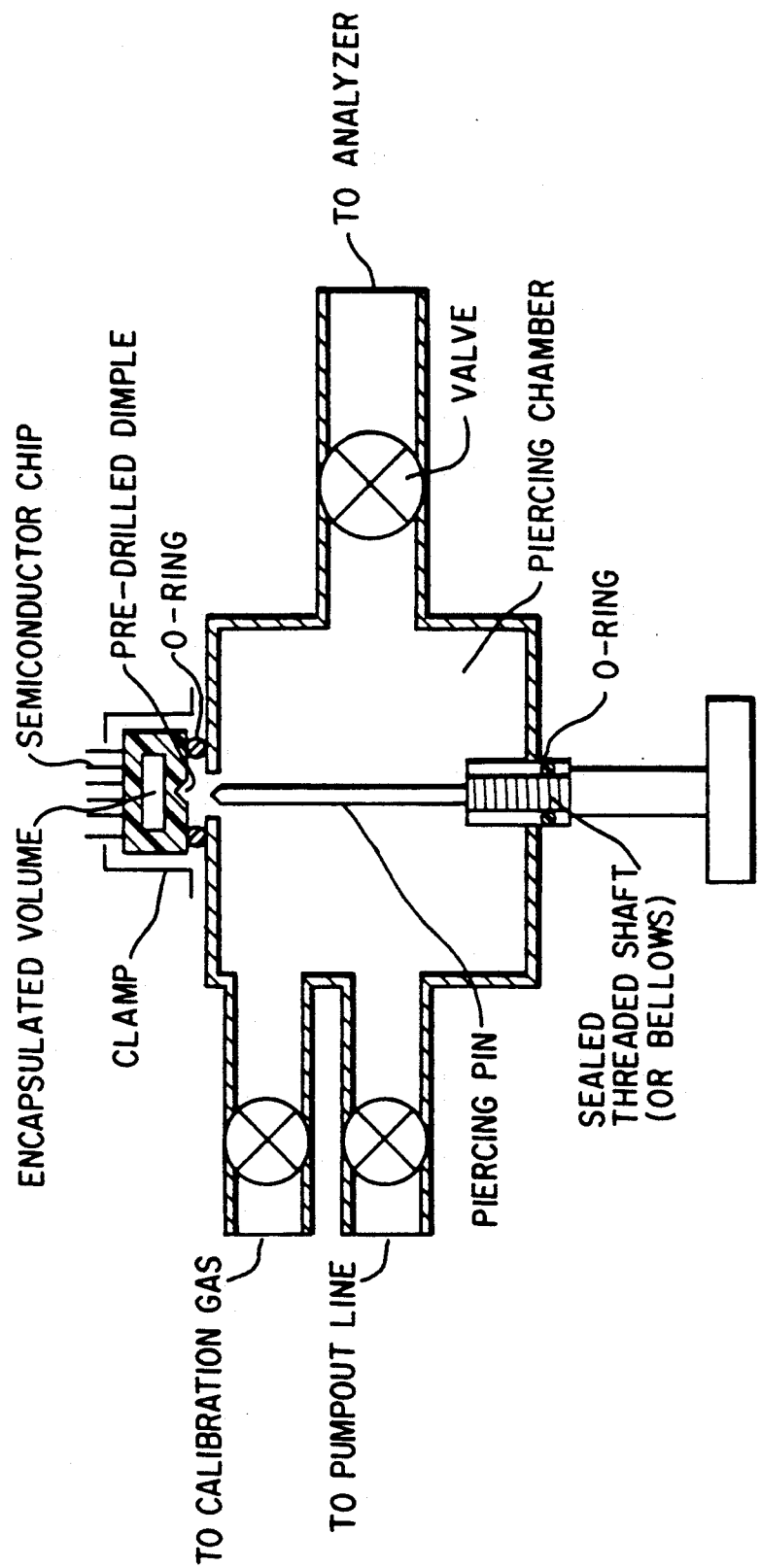
FIG. 1 is a diagrammatic sectional side view of a typical prior art embodiment.
Figure 2:
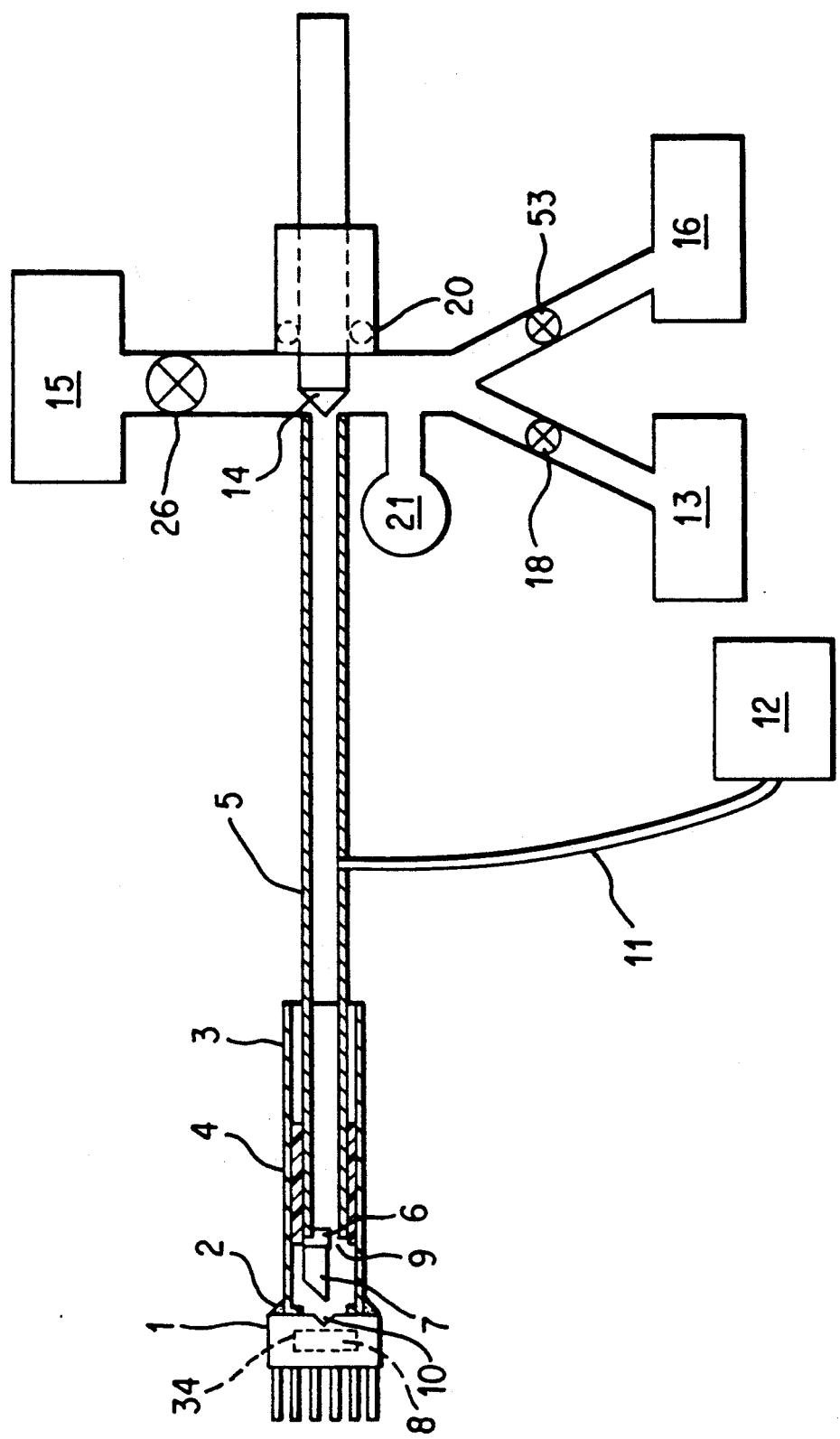
FIG. 2 is a diagrammatic sectional view illustrating a basic embodiment of the instant invention.

Referring, in particular, to FIG. 2, an encapsulated object 1, which is depicted as a microelectronic component, but which may be a piece of glass containing a bubble, or other confined space confining a fluid, is glued in a rugged, vacuum-tight seal, via a bead of high-grade epoxy 2 onto the end of a tube 3, the inner surface of which is equipped with a sealable, slidable gasket or ferrule 4 composed of Teflon or a similar material, the purpose of which is to permit a slidable seal with an internally disposed tub 5, which may be compose of electropolished/heat-treated stainless steel, glass or other materials which those skilled in the art consider is suitable for such use. On one end of the internally disposed tube 5, retained via a mechanical crimp mount 6, is a piercing pin 7, oriented so that, when said tube 3 is slid to the right as seen in FIG. 2, piercing pin 7 contacts, shatter, drills or otherwise punctures or ruptures the exposed side of object 1, allowing its contents 8 of cavity 34 to emerge into tube 5 via a small passage 9 in mechanical crimp mount 6. The puncturing process is facilitated by the existence of a notch, depression or dent 10 previously pressed, carved, drilled or ground into the surface of object 1 prior to said object 1 being epoxied onto tube 3.

Contents 8, upon being freed from their confined space in object 1, flow into the tube 5 through passage 9, adjacent piercing pin 7, and are received into capillary 11, which is about fifty micrometers in diameter and ten to twenty inches in length and which is composed of fused silica glass or the like. Capillary 11 carried the fluid to an analyzing device 12, which is a mass spectrometer, infrared analyzer or the like. When analysis of contents 8 via analyzer 12 is sufficiently complete, the internally disposed tube 5 is evacuated by opening valve 14. Valve 14 is preferably a metal-to-metal seating type that, when closed, presents no elastomer surfaces that might sorb any gaseous species constituent to said contents 8. Valve 14 furthermore is of a type that, when open, permits the internally disposed tube 5 to be evacuated, flushed with calibration gas, or subjected to other procedures understood by those skilled in the art.

Figure 3:
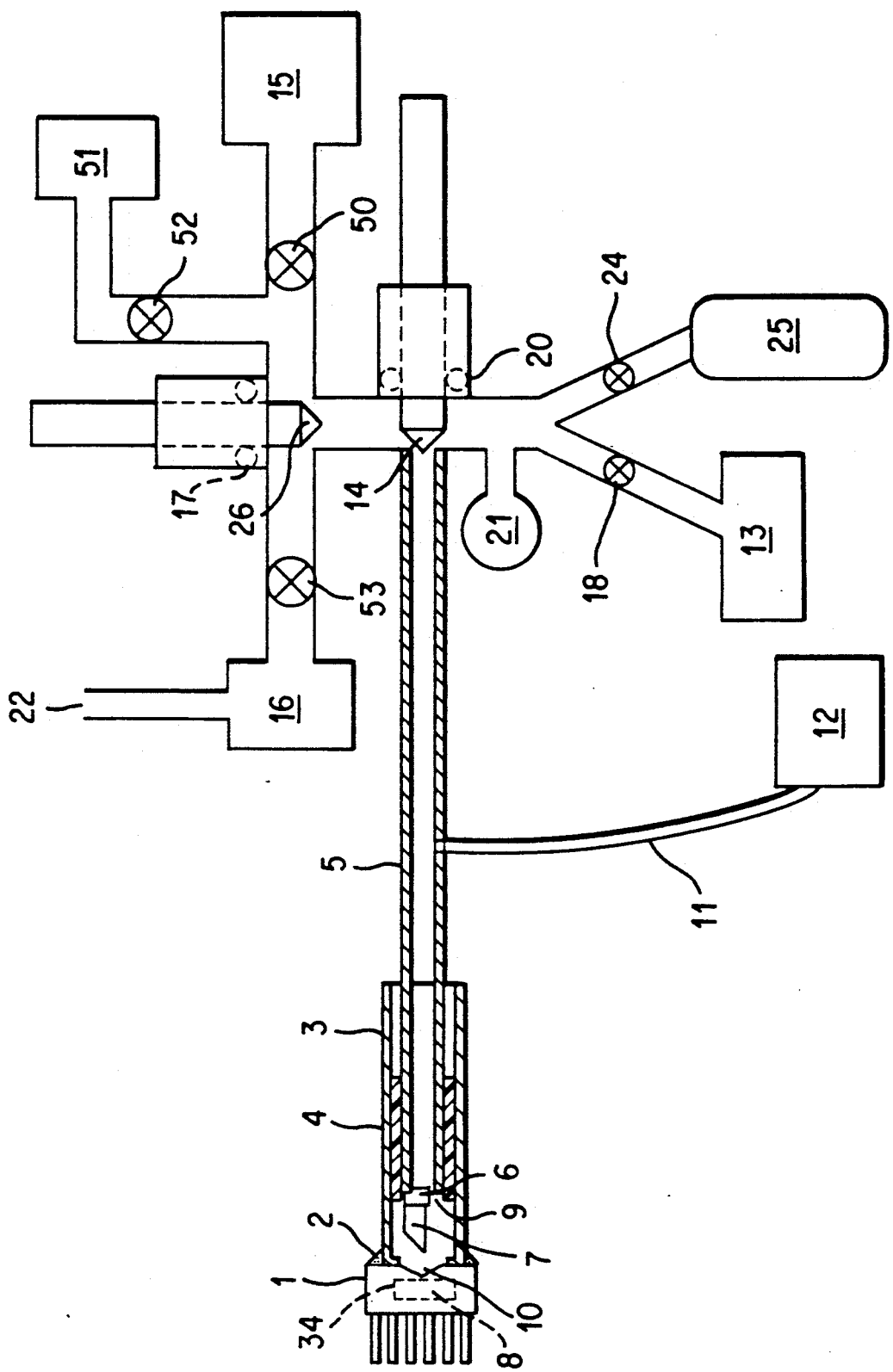
FIG. 3 is a diagrammatic sectional side view of a preferred embodiment of the invention.

FIG. 3 shows an alternative of the subject invention in which calibration gases from source 15, which may be bottled gases or humidified bottled gases or other such mixtures well-known in the art, are flushed past valve 50 and then through a second valve 26 similar to valve 14, the purpose of said valve 26 being to allow gas source 15 to purge continuously through calibration analyzer 16 and its control valve 53 and vent to atmospheric dump 22 independently of operation of all other portions of the system. In addition, a dry purge gas source 51, along with its control valve 52, is installed in parallel to calibration gas source 15. Further, there is added a dry gas ballast source 25 which is coupled to the pump-out line for pump 13 via a pressure regulator 24 for the purpose of allowing more precise control of the pressure in the vicinity of valve 14 with a higher overall gas load to pump 13 via restrictive valve 18. Calibration analyzer 16 may be a dew point analyzer (in the case of water) or other such analyzers that are able to monitor gross quantities of those gases of interest for a specific application. Because large quantities of calibration gas are being purged through the aforedescribed system, the effect of adsorption by valves 50 and 52 and by the elastomer O-rings 20 and 17 needed to seal valves 26 and 14 are effectively swamped out by the large quantity of gas from said gas source 15.

Typical operation using the embodiment shown in FIG. 3 is as follows. First the system may be operated in a standby or purge condition, prior to mounting the encapsulated object 1 epoxied to its tube 3, in which valves 52, 26 and 14 are opened and all other valves are closed. Under this condition, dry purge gas continuously flows through and out the open end of the internally disposed tube 5, preventing atmospheric moisture or other contaminants from entering inner tube 5 and capillary 11. Encapsulated object 1, as epoxied to its tube 3, is mounted onto internally disposed tube 5 and sealed via slidable Teflon gasket 4, while said purge is taking place. Following said sealing, the system may be placed into a cleanup pumpdown by opening valve 18 to vacuum pump 13 so as to evacuate tube 5 through open valve 14. Pressure regulator 24 is used in conjunction with ballast gas source 25 as described above. Under this condition, the system is pumped to a moderate vacuum with continuous purging by dry purge gas source 51 via partially opened leak valve 26. Following approximately thirty seconds of said cleanup pumpdown, the system is placed into a hard pumpdown by completely closing valve 26 and regulator 24 for another thirty seconds. At this point, the contents 8 of encapsulated object 1 may be sampled by closing valve 14 and breaking through object 1 at notch 10 with pin 7 as previously described.

Figure 4:
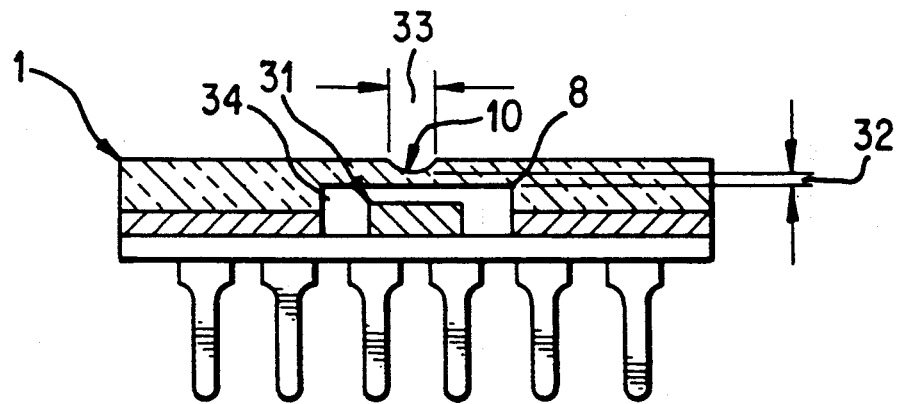
FIG. 4 is a sectional side view of a typical ceramic integrated circuit microchip illustrating the process.

FIG. 4 is a side view of a typical ceramic integrated circuit microchip 1 in which the actual integrated circuit 31 is shown encapsulated within a cavity in the device 1, said cavity containing the gas 8 which is to be sampled. Dimple or notch 10 is shown as having a typical width 33 of 0.12 inch and a depth such that approximately 0.005 to 0.015 inch of material 32 remains to be pierced.

Figure 5:
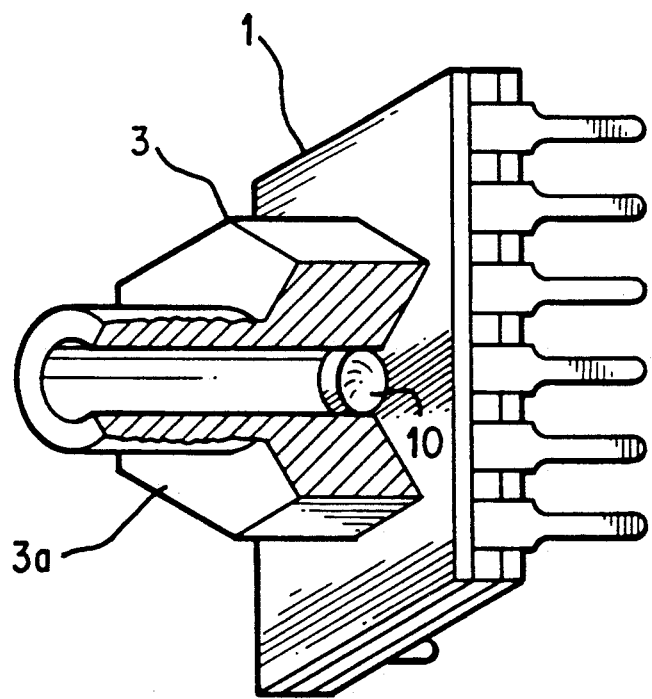
FIG. 5 is a perspective view showing the use of a standard vacuum plumbing fitting shown in partial section as the piercing chamber header.

FIG. 5 is a perspective drawing showing the tube 3 as actually consisting of a slightly modified standard stainless steel vacuum fitting 3a marketed under the trademark Swagelock, fitting 3a being epoxied onto an integrated circuit microchip 1 such that the hole through fitting 3a is aligned with notch or depression 10. Fitting 3a may be a Swagelock Cap SS-200-C stainless fitting, drilled out to provide a passage to object 1 and to accommodate the internally disposed tube 5 which has a one-eighth inch outside diameter (not shown in FIG. 5).

Figure 6:
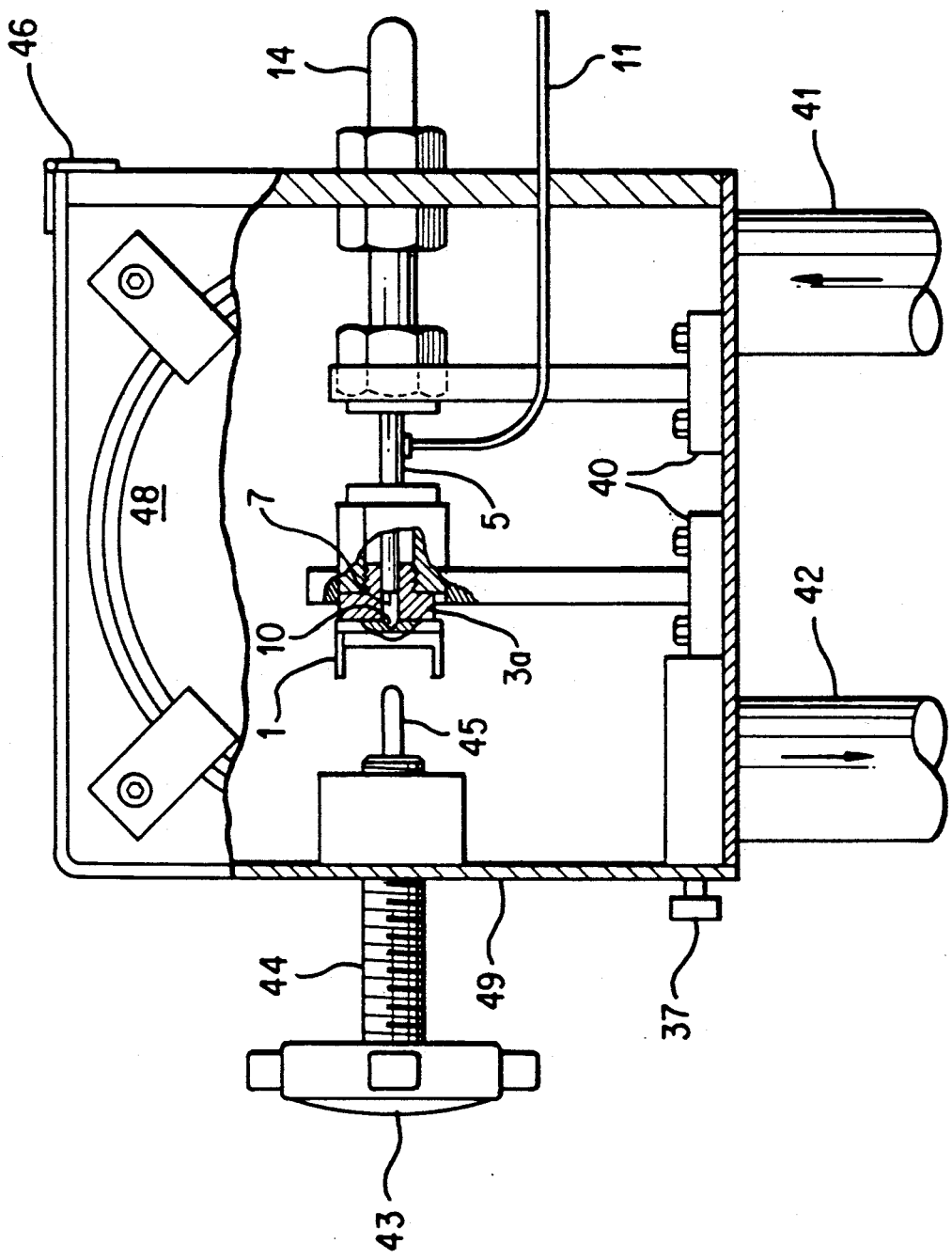
FIG. 6 depicts in partial cross-section use of the invention as part of a heated inlet system assembly, a portion being cut away to disclose the disposition of the fitting shown in FIG. 5 in the assembly.

FIG. 6 depicts a typical application of the invention in which encapsulated object 1 epoxied onto fitting 3a is sealed onto internally disposed tube 5 fitted with fused silica capillary sampling tube 11, all of which are supported by brackets 40 to the assembly inside a heat chamber comprising a box 49 through which heated air may be selectively circulated via inlet port 41 and outlet port 42 while permitting rupture of, or penetration into, object 1 via notch 10 by moving push rod 45 driven by threaded rod 44 turned by handle 43. Hinge 46 permits easy access via removal of bolt 37 to the apparatus for exchanging encapsulated objects, while a transparent viewport 48 facilitates operation by permitting the operator to view the various parts of the assembly within box 49.

Other procedures for use and calibration of the overall system, such as repeated purge and hard pumpdown cycles, multi-point calibration, and the use of analyzers other than quadrupole mass filters, will be apparent to those skilled in the art.

It is important to understand that it is an object of the invention to obtain essentially viscous flow of the gaseous contents 8 which flow from the cavity 34 from the rupture at notch 10 and that this is accomplished by reducing insofar as reasonably practicable the interior volume of the passageway from the rupture through notch 10 through the passage 9, and the internally disposed tube 5. In this manner, all of the molecules of interest in the gaseous contents 8 are carried with the flow and are not separated according to molecular weight by transition or molecular flow. A second important object of the invention is to reduce insofar as possible the surface area available for adsorption of constituents of the gaseous sample and furthermore to have even those reduced surfaces contain no materials known to be strong adsorbers of any of the gases of interest, water being the best-known example. Of course, this may not always be possible, such as wherein analysis of molecules adsorbed within cavity 34 are also of interest. However, the invention is also adaptable to analyze the latter constituents by baking out or other procedures employed to desorb the molecules which had earlier been adsorbed by the interior surfaces of cavity 34. To ensure that a viscous flow regime exists from the rupture into cavity 34 through the internally disposed tube 5 and as far as the entry into capillary 11 is important and it is necessary that the pressure within the just-mentioned spaces be relatively high.

Accordingly, although we have described the preferred embodiments of our invention, it is to be understood that it is capable of other adaptations and modifications within the scope of the appended claims.

Having thus disclosed our invention, what we claim as new and desire to secure by Letters Patent of the United States is:

1. A method of analyzing the composition of a small volume of fluid that is initially confined in a small space in an object, said method comprising penetrating said object so that said fluid emerges into a sample chamber, limiting the amounts of said fluid which are sorbed by the interior surfaces of said sample chamber to inconsequential amounts by providing that said sample chamber is sufficiently small to achieve this result, and retaining the fluid that emerges from said space at a pressure in said sample chamber that is sufficiently high so that essentially viscous flow and/or steady state flow conditions exist in said sample chamber and all passages that conduct said fluid to an analyzer so that said analyzer is therefore able to measure in real time the relative composition of the chemical constituents of said fluid via the ratio of real-time measurements of individual constituents of said fluid.

2. A method in accordance with claim 1, including the further step of heating said object and said fluid confined therein, said sample chamber and said passages sufficiently to ensure that said fluid remains in a vapor phase therein.

3. A method in accordance with claim 2, wherein said heating step sufficiently reduces substantial adsorption of said fluid in the vapor phase by said object, said sample chamber and said passages.

4. A method in accordance with claim 1, for use with a said fluid containing a species that is prone to be adsorbed onto said interior surfaces whereby the amount of said species so adsorbed in the process is minimized.

5. A method in accordance with claim 1, wherein said confined fluid is composed in part of water.

6. A method in accordance with claim 1, wherein said object is an electronic device which includes an encapsulated space and wherein the water vapor content of said encapsulated space is consequential to the intended operations of said device.

7. A method in accordance with claim 6, wherein said object is a transistor.

8. A method in accordance with claim 6, wherein said object is a solid-state integrated circuit.

9. A method in accordance with claim 1, wherein said confined space comprises a bubble and the analysis of content of said bubble is consequential for control of a process of manufacture.

10. An apparatus for analysis of the contents of small encapsulated volumes in solid objects, said apparatus comprising a fitting which is adapted to be glued onto an object containing fluids in said encapsulated volumes which are to be analyzed, said fitting being equipped with a slidable seal that hermetically seals therein a small tube, said small tube comprising a piercing device adapted to penetrate into said object when said fitting with said object glued thereon is moved into contact with said piercing device to rupture said object sufficiently so that the contents of said encapsulated emerge into said small tube, said small tube being of sufficiently small size that the pressure in said small tube after said contents emerge therein remain sufficiently high that essentially viscous flow and/or steady-state flow conditions exist in said small tube and sorption effects on said contents are inconsequential.

11. An apparatus in accordance with claim 10, wherein said small tube is connected to a capillary tube composed of fused silica or the equivalent, said capillary adapted to conduct said contents from said small tube to an analyzing device.

12. An apparatus in accordance with claim 11, wherein no materials are present in said small tube and said flow passages which adsorb vapors of interest from said contents as said contents are conducted from said object to said analyzing device.

13. An apparatus in accordance with claim 12, wherein no elastomer O-rings or gaskets are present in said small tube and said flow passages.

14. An apparatus in accordance with claim 10, comprising additional fittings and valves, connected to said small tube for pre-evacuating all fluids in the flow passages between said object and said analyzing device, so that after the contents of said encapsulated volumes emerge into said small tube and are conducted through said flow passages to said analyzing device, substances not present in said contents are present only in inconsequential amounts when received by said analyzing device.

15. An apparatus in accordance with claim 10, including means for conducting known mixtures of gases to said small tube for the purpose of calibrating said analyzing device.

16. An apparatus in accordance with claim 10, wherein the interior volume of said small tube is not greater than 0.04 cubic centimeters.

17. An apparatus in accordance with claim 10, which comprises a heating chamber into which said object, said small tube and said capillary are installed.

18. An apparatus in accordance with claim 10, wherein said object is a solid-state electronic device.

19. An apparatus in accordance with claim 18, wherein the contents of said encapsulated volumes include water.

20. An apparatus in accordance with claim 19, wherein said fitting is adapted to be glued onto said object by epoxy cement.

21. An apparatus in accordance with claim 10, wherein said piercing device is a hardened pin.

22. An apparatus in accordance with claim 21, wherein said metal-to-metal valve is coupled to means for supplying a calibration gas with a composition and pressure similar to the contents of said encapsulated volume.

23. An apparatus in accordance with claim 10, comprising a metal-to-metal valve fitted on an end of said small tube opposite to where said small tube is adapted to be glued to said object, said valve adapted to isolate said small tube so that no surfaces composed of substances known to adsorb any fluids of interest for analysis are presented to said contents while they are conducted from said object to said analyzing device.

24. An apparatus in accordance with claim 10, wherein said capillary is composed of fused silica.

25. An apparatus in accordance with claim 10, wherein said small tube is composed of electropolished steel.

26. An apparatus in accordance with claim 10, wherein said small tube is composed of a heat-treated stainless steel.

27. An apparatus in accordance with claim 10, wherein said small tube is composed of glass, ceramic or similar material.

28. An apparatus in accordance with claim 10, wherein said analyzing device comprises a quadrupole mass spectrometer.

29. An apparatus for analysis of the contents of small encapsulated volumes in solid objects, said apparatus comprising a fitting adapted to be glued onto an object containing encapsulated gases the composition of which are to be analyzed, said fitting being equipped with a slidable seal hermetically sealing onto the inner surface of said fitting a small tube, said small tube being equipped with a piercing device for providing an opening through said side of said object when said fitting with said glued-on object is slid via said slidable seal against said piercing device whereby contents of said encapsulated volume flow into said small tube, said small tube being of sufficiently small volume that subsequent pressure in said small tube remains sufficiently high for viscous flow conditions and that sorption or desorption effects are inconsequential, said small tube connecting to a capillary tube composed of quartz glass or the like, said capillary serving to transport said encapsulated gas to an analyzing device, said small tube being further provided with additional fittings and valves for pre-evacuating all gas and vapor so that subsequent to release of said encapsulated gas from said object, substantially no substances other than those originally present in said encapsulation remain in said small tube, said additional fittings and valves being composed effectively substantially of materials which will not adsorb gases of interest in said encapsulated gases prior to transport said gases via capillary to said analyzer, said fittings and valves being constructed and arranged so that said small tube may be evacuated and then filled with known mixtures of gases for the purpose of calibrating said analyzer.

30. Apparatus in accordance with claim 29 wherein the interior volume of said small tube is no greater than 0.01 cubic centimeters.

31. Apparatus in accordance with claim 30 wherein said object is a solid-state electronic device.

32. Apparatus in accordance with claim 31 wherein $H_2O$ is included within said encapsulated volume.

33. Apparatus in accordance with claim 29 wherein said apparatus is installed inside a heated chamber.

34. Apparatus in accordance with claim 29 wherein said piercing device comprises a needle.

35. Apparatus in accordance with claim 34 wherein said metal-to-metal valve is also coupled to a supply of calibration gas with composition similar to gas in said encapsulated volumes adapted periodically to flood said small tube with said calibration gas at controlled pressures to enable a user to calibrate the overall system.

36. Apparatus in accordance with claim 29 wherein epoxy cement is provided for gluing said object to said fitting.

37. Apparatus in accordance with claim 29 wherein said small tube is fitted at its end opposite to said encapsulated object with a metal-to-metal valve whereby the interior volume of said small tube may be isolated so that no surfaces made of elastomers or other materials known to adsorb substances of interest from said encapsulated volumes are presented to said encapsulated gases prior to their transport via said capillary tube to said analyzer.

38. Apparatus in accordance with claim 29 wherein said capillary tubing is composed of fused silica.

39. Apparatus in accordance with claim 29 wherein said small tube is composed of electro-polished or heat-treated stainless steel.

40. Apparatus in accordance with claim 29 wherein said small tube is composed of glass.

41. Apparatus in accordance with claim 36 wherein said analyzer comprises a quadrupole mass spectrometer.

* * * * *